United States Patent
Ueda et al.

(10) Patent No.: US 11,877,726 B2
(45) Date of Patent: Jan. 23, 2024

(54) ENDOSCOPE AID AND ENDOSCOPE CAPABLE OF CHANGING INTERNAL DIAMETER OF TREATMENT TOOL INSERTION CHANNEL

(71) Applicant: FUJIFILM Corporation, Tokyo (JP)

(72) Inventors: Yoshihiro Ueda, Kanagawa (JP); Nobuyuki Torisawa, Kanagawa (JP); Shozo Iyama, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 406 days.

(21) Appl. No.: 17/138,911

(22) Filed: Dec. 31, 2020

(65) Prior Publication Data

US 2021/0121054 A1 Apr. 29, 2021

Related U.S. Application Data

(63) Continuation of application No. PCT/JP2019/031558, filed on Aug. 9, 2019.

(30) Foreign Application Priority Data

Aug. 16, 2018 (JP) .................................. 2018-153161

(51) Int. Cl.
- *A61B 1/00* (2006.01)
- *A61B 1/015* (2006.01)
- *A61B 1/018* (2006.01)

(52) U.S. Cl.
CPC ...... *A61B 1/00119* (2013.01); *A61B 1/00101* (2013.01); *A61B 1/00128* (2013.01);
(Continued)

(58) Field of Classification Search
CPC ............ A61B 1/00119; A61B 1/00101; A61B 1/00128; A61B 1/015; A61B 1/018; A61B 1/012; A61B 1/0052; A61B 1/0055
(Continued)

(56) References Cited

U.S. PATENT DOCUMENTS

| 4,972,828 A | 11/1990 | Ito |
| 8,827,897 B2* | 9/2014 | Sato ................. A61B 1/0052 |
| | | 600/149 |

(Continued)

FOREIGN PATENT DOCUMENTS

| CN | 106455925 | 2/2017 |
| CN | 106470589 | 3/2017 |

(Continued)

OTHER PUBLICATIONS

"International Search Report (Form PCT/ISA/210)"of PCT/JP2019/031558, dted Nov. 5, 2019, with English translation thereof, pp. 1-5.
(Continued)

*Primary Examiner* — John P Leubecker
*Assistant Examiner* — Li-Ting Song
(74) *Attorney, Agent, or Firm* — JCIPRNET

(57) ABSTRACT

An endoscope aid is attachably and detachably attached to a treatment tool insertion channel of an endoscope where a suction tube joins. The endoscope aid includes a flexible tubular member having a length equal to or larger than a length ranging from at least an inlet-side end part of an outlet portion of the treatment tool insertion channel, which is maintained in the shape of a straight pipe regardless of bending of a bending part of the endoscope, to an inlet of the treatment tool insertion channel. The tubular member has a distal end part that has an outer periphery in sliding contact with an inner peripheral surface of the outlet portion of the treatment tool insertion channel and is disposed at the outlet portion, and a communication part that allows an outlet of the treatment tool insertion channel and the suction tube to communicate with each other.

11 Claims, 12 Drawing Sheets

(52) U.S. Cl.
CPC .......... *A61B 1/00147* (2013.01); *A61B 1/015* (2013.01); *A61B 1/018* (2013.01)

(58) Field of Classification Search
USPC ........................................ 600/104, 139, 156
See application file for complete search history.

(56) References Cited

U.S. PATENT DOCUMENTS

| | | |
|---|---|---|
| 2007/0255105 A1 | 11/2007 | Ochi et al. |
| 2008/0287961 A1 | 11/2008 | Miyamoto et al. |
| 2011/0251458 A1 | 10/2011 | Terliuc et al. |
| 2012/0172667 A1* | 7/2012 | Takeuchi .............. A61B 1/0055 600/140 |
| 2013/0274550 A1* | 10/2013 | Takeuchi ............... A61B 1/015 600/104 |
| 2014/0100463 A1* | 4/2014 | Sekiguchi ............. A61B 1/018 600/103 |
| 2015/0230692 A1* | 8/2015 | Matsuda ............ A61B 1/00096 600/110 |
| 2017/0027415 A1* | 2/2017 | Terliuc ............... A61B 1/00082 |
| 2017/0079505 A1 | 3/2017 | Nakade |
| 2017/0086652 A1 | 3/2017 | Nakade et al. |
| 2017/0265723 A1 | 9/2017 | Yamaya |
| 2019/0246885 A1 | 8/2019 | Karikomi et al. |

FOREIGN PATENT DOCUMENTS

| | | | |
|---|---|---|---|
| EP | 1955643 | | 8/2008 |
| EP | 3216380 | | 9/2017 |
| JP | 2001231746 | | 8/2001 |
| JP | 2001231746 A | * | 8/2001 |
| JP | 2002330925 | | 11/2002 |
| JP | 2008054786 | | 3/2008 |
| WO | 2012005124 | | 1/2012 |
| WO | 2018088087 | | 5/2018 |

OTHER PUBLICATIONS

"Written Opinion of the International Searching Authority (Form PCT/ISA/237)" of PCT/JP2019/031558, dated Nov. 5, 2019, with English translation thereof, pp. 1-7.

"Search Report of Europe Counterpart Application", dated Aug. 31, 2021, p. 1-p. 7.

"Office Action of China Counterpart Application", dated Oct. 20, 2023, with English translation thereof, p. 1-p. 14.

* cited by examiner

ENDOSCOPE AID AND ENDOSCOPE CAPABLE OF CHANGING INTERNAL DIAMETER OF TREATMENT TOOL INSERTION CHANNEL

CROSS-REFERENCE TO RELATED APPLICATIONS

This application is a Continuation of PCT International Application No. PCT/JP2019/031558 filed on Aug. 9, 2019, which claims priority under 35 U.S.C § 119(a) to Japanese Patent Application No. 2018-153161 filed on Aug. 16, 2018. Each of the above application(s) is hereby expressly incorporated by reference, in its entirety, into the present application.

BACKGROUND OF THE INVENTION

1. Field of the Invention

The present invention relates to an endoscope aid and an endoscope.

2. Description of the Related Art

A treatment tool insertion channel protective device described in JP2001-231746A has almost the same length as the length of a treatment tool insertion passage of an endoscope and comprises a flexible protective tube capable of being inserted into and removed from the treatment tool insertion passage, and a proximal end mouthpiece coupled to a proximal end of the protective tube. The proximal end mouthpiece is engageable with and disengageable from an inlet portion of the treatment tool insertion passage and has an inner hole that smoothly communicates with the protective tube.

SUMMARY OF THE INVENTION

The internal diameters of treatment tool insertion channels of endoscopes are variously different. For example, the internal diameter of a treatment tool insertion channel of an oral endoscope is larger than the internal diameter of a treatment tool insertion channel of a transnasal endoscope. The sizes of treatment tools are variously different. For example, there is a case where a treatment tool with a relatively small size is preferably used for the treatment that requires an accurate treatment tool operation. Here, in a case where the internal diameter of a treatment tool insertion channel is excessive with respect to the size of a treatment tool, the disposition of the treatment tool is not settled in an outlet portion of the treatment tool insertion channel, and the difficulty of treatment increases unnecessarily. On the other hand, changing endoscopes in accordance with treatment imposes a burden on a subject. Therefore, in one endoscope, the internal diameter of a treatment tool insertion channel is desired to be changed depending on situations.

The treatment tool insertion channel protective device described in JP2001-231746A is intended to insert and remove a treatment tool such as a puncturing needle into and from the treatment tool insertion passage of the endoscope without obstruction. However, the internal diameter of the treatment tool insertion channel is changed by the protective tube having almost the same length as the length of the treatment tool insertion passage. However, the disposition of the protective tube in the outlet portion of the treatment tool insertion channel is not taken into consideration at all. In a case where the disposition of the protective tube is not stable at the outlet portion of the treatment tool insertion channel, the disposition of the treatment tool inserted through the protective tube is not stable.

In a case where the difference between the internal diameter of the treatment tool insertion channel and the external diameter of the protective tube is set to be extremely small such that the disposition of the protective tube at the outlet portion of the treatment tool insertion channel is stable, the inner hole of the treatment tool insertion channel is blocked by the protective tube. Generally, a suction tube joins the treatment tool insertion channel, and the treatment tool insertion channel is also used for suction of a liquid such as blood. In a case where the inner hole of the treatment tool insertion channel is blocked by the protective tube, suction cannot be performed.

The present invention has been made in view of the above-described circumstances, and an object thereof is to provide an endoscope aid capable of changing the internal diameter of a treatment tool insertion channel of an endoscope in accordance with situations, stabilizing the disposition of a treatment tool in the outlet portion of the treatment tool insertion channel, and capable of performing suction, and an endoscope comprising a treatment tool insertion channel to which the endoscope aid is attachable.

The endoscope aid of an aspect of the present invention is an endoscope aid to be attachably and detachably attached to a treatment tool insertion channel of an endoscope where a suction tube joins. The endoscope aid comprises a flexible tubular member having a length equal to or larger than a length ranging from at least an inlet-side end part of an outlet portion of the treatment tool insertion channel, which is maintained in a shape of a straight pipe regardless of bending of a bending part of the endoscope, to an inlet of the treatment tool insertion channel. The tubular member has a distal end part that has an outer periphery in sliding contact with an inner peripheral surface of the outlet portion of the treatment tool insertion channel and is disposed at the outlet portion, and a communication part that allows an outlet of the treatment tool insertion channel and the suction tube to communicate with each other.

Additionally, an endoscope of an aspect of the present invention comprises a treatment tool insertion channel to which the endoscope aid is attachable.

According to the present invention, it is possible to provide the endoscope aid capable of changing the internal diameter of the treatment tool insertion channel of the endoscope in accordance with situations, stabilizing the disposition of the treatment tool in the outlet portion of the treatment tool insertion channel, and performing suction and it is possible to provide the endoscope comprising the treatment tool insertion channel to which the endoscope aid is attachable.

DESCRIPTION OF THE PREFERRED EMBODIMENTS

Figure 1:
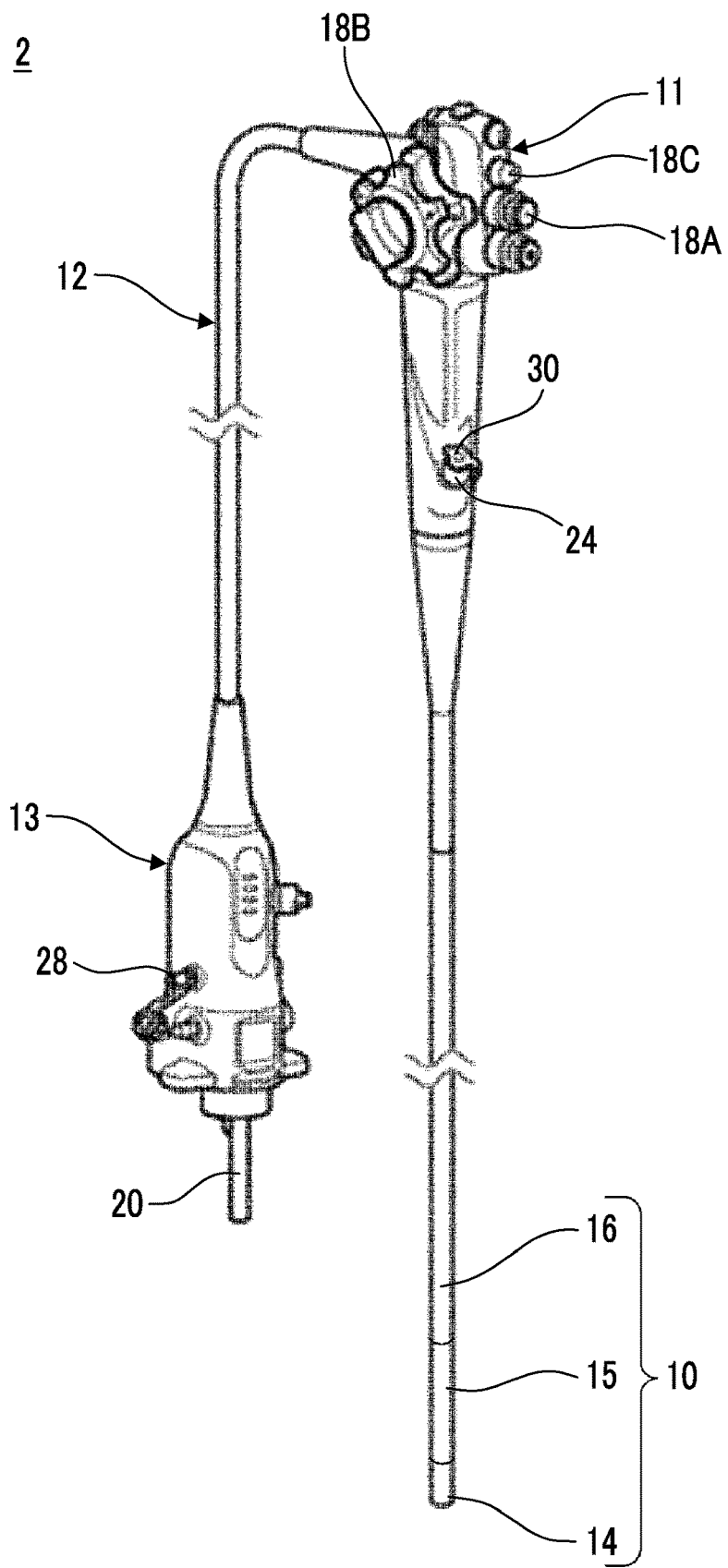
FIG. 1 is a perspective view of an example of an endoscope for explaining an embodiment of the present invention.
Figure 2:
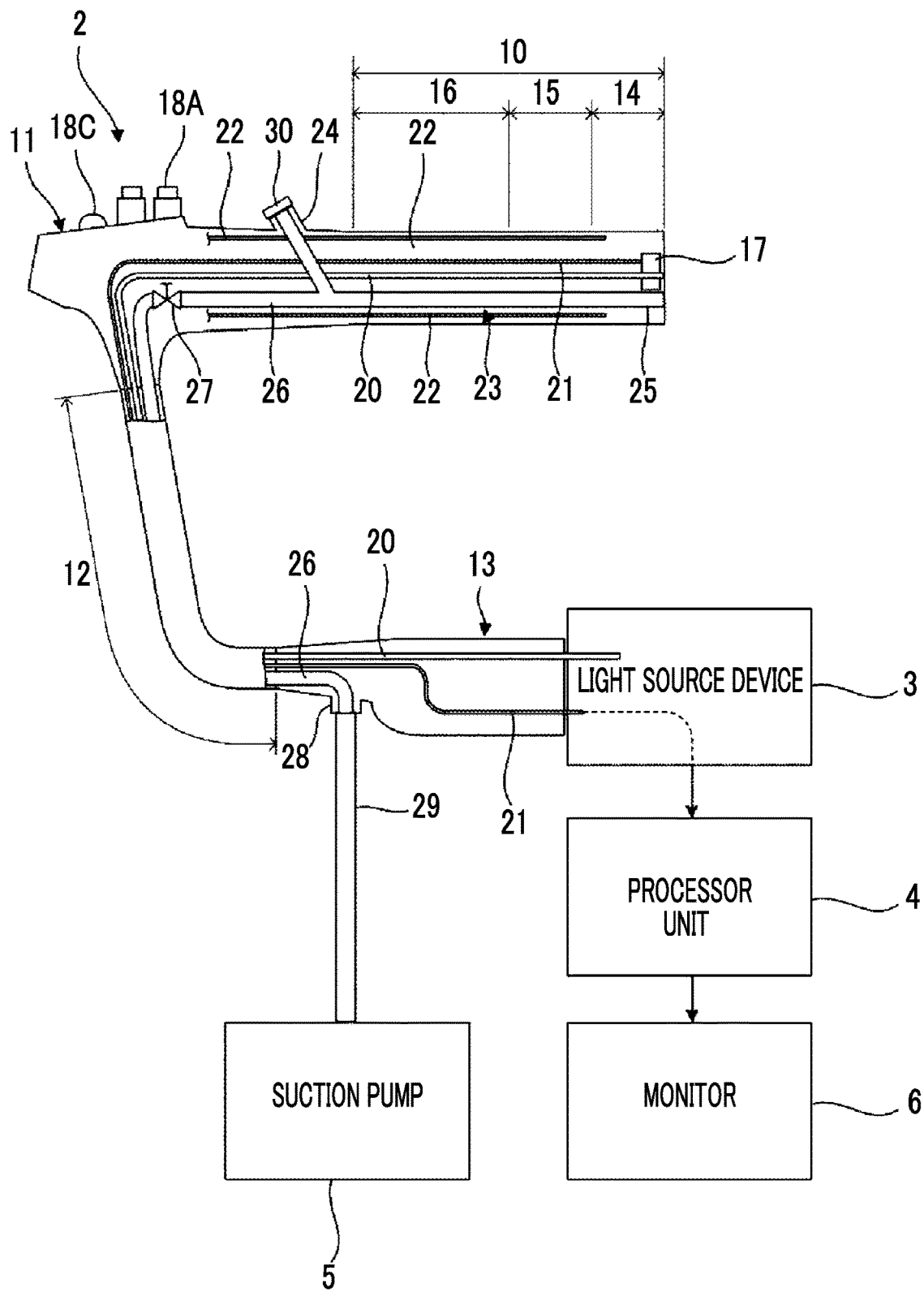
FIG. 2 is a schematic view of an example of an endoscope system including the endoscope of FIG. 1.

FIG. 1 illustrates an example of an endoscope for explaining an embodiment of the present invention, and FIG. 2 illustrates an example of an endoscope system including the endoscope of FIG. 1.

The endoscope system 1 comprises an endoscope 2, a light source device 3, a processor unit 4, and a suction pump 5. An endoscope 2 has an insertion part 10 to be inserted into a subject, an operating part 11 connected to the insertion part 10, and a universal cord 12 extending from the operating part 11, and a terminal of the universal cord 12 is provided with a connector 13 to be connected to the light source device 3.

The insertion part 10 is constituted of a distal end part 14, a bending part 15 connected to the distal end part 14, and a flexible part 16 that connects the bending part 15 and the operating part 11 to each other. An imaging unit 17 including imaging elements, such as a charge coupled device (CCD) image sensor and a complementary metal oxide semiconductor (CMOS) image sensor, is mounted on the distal end part 14. The bending part 15 is configured to be bendable, and bending of the bending part 15 is operated by the operating part 11. Additionally, the flexible part 16 is configured to be flexible so as to be deformable along the shape of an insertion path of the subject.

The operating part 11 is provided with an operation button 18A that operates suction using the suction pump 5, an operating knob 18B that operates the bending of the bending part 15, an operation button 18C that operates imaging using the imaging unit 17, and the like. Additionally, the operating part 11 is provided with an inlet portion 24 of the treatment tool insertion channel 23 through which a treatment tool is inserted.

A light guide 20 and an electrical cable 21 are provided inside the insertion part 10, the operating part 11, and the universal cord 12. The light guide 20 guides illumination light, which is to be generated by the light source device 3, to the distal end part 14. The electrical cable 21 transmits operating power, control signals, and captured image signals of the imaging unit 17 between the imaging unit 17 and the processor unit 4. The processor unit 4 generates captured image data from input captured image signals, and causes the generated captured image data to be displayed on the monitor 6 and recorded.

A plurality of operating wires 22 and a treatment tool insertion channel 23 are provided inside the insertion part 10 and the operating part 11. The operating wires 22 reach the distal end part 14 of the insertion part 10 from the operating part 11, and are pushed toward the distal end part 14 or pulled toward the operating part 11 in accordance with the operation of the operating knob 18B of the operating part 11. The bending part 15 of the insertion part 10 is bent in accordance with the push/pull of the operating wire 22. The treatment tool insertion channel 23 reaches the distal end part 14 of the insertion part 10 from the inlet portion 24 provided in the operating part 11, and an outlet portion 25 of the treatment tool insertion channel 23 opens to an end surface of the distal end part 14. A treatment tool inserted into the treatment tool insertion channel 23 through the opening of the inlet portion 24 is guided to the distal end part 14 of the insertion part 10 by the treatment tool insertion channel 23 and protrudes from the distal end part 14 through an opening of the outlet portion 25.

The treatment tool insertion channel 23 joins a suction tube 26 in the operating part 11. The suction tube 26 extends to the connector 13 via a valve 27 opened and closed by the operation button 18A and is connected to the suction pump 5 via the connection tube 29 connected to a mouthpiece 28 provided in the connector 13. By opening the valve 27, the liquid, such as blood, is suctioned from the opening of the outlet portion 25 of the treatment tool insertion channel 23 to the suction pump 5 through the suction tube 26. In addition, a forceps valve 30 having an on-off valve is mounted on the inlet portion 24, and as the opening of the inlet portion 24 is closed by the forceps valve 30 at the time of suction, the internal pressure of the treatment tool insertion channel 23 becomes negative pressure.

Figure 3:
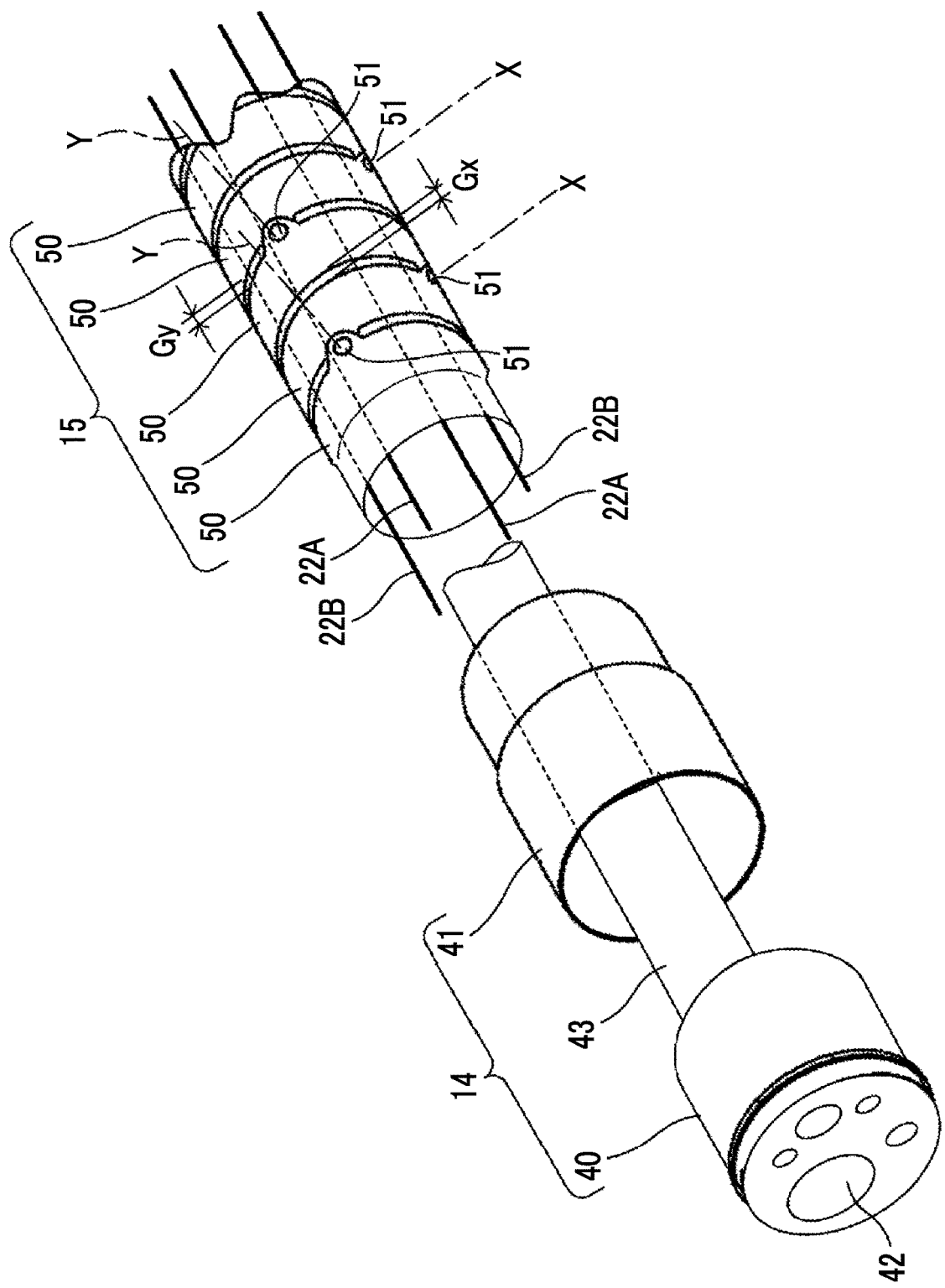
FIG. 3 is a perspective view illustrating an internal mechanism of a distal end part and a bending part of an insertion part of the endoscope of FIG. 1.

FIG. 3 illustrates an internal mechanism of the distal end part 14 and the bending part 15 of the insertion part 10.

The distal end part 14 has a columnar distal end rigid part 40 that holds various built-in elements, such as the imaging unit 17 (refer to FIG. 2), to be mounted on the distal end part 14, and a cylindrical distal end sleeve 41 to be fixed to a proximal end side of the distal end rigid part 40. A through-hole 42, which penetrates the distal end rigid part 40 in an axial direction and has a circular cross-sectional shape, is formed in the distal end rigid part 40. A flexible channel tube 43, which constitutes the treatment tool insertion channel 23 and has a circular cross-sectional shape, is joined to the distal end rigid part 40. An inner hole of the channel tube 43 joined to the distal end rigid part 40, and the through-hole 42 communicate with each other, and the through-hole 42 constitutes at least a portion of the outlet portion 25 of the treatment tool insertion channel 23.

The bending part 15 has a plurality of annular pieces 50, and the pieces 50 are arranged with their central axes aligned with each other. A piece 50 disposed nearest to the distal end part 14 side among the plurality of pieces 50 is fixed to the distal end sleeve 41 of the distal end part 14. Two adjacent pieces 50 are coupled to each other so as to be rotationally movable by a pair of shaft members 51 disposed on an axis orthogonal to a longitudinal axis of the bending part 15. As the rotational movements of the two adjacent pieces 50 are combined together, the bending part 15 is bent as a whole.

In the example illustrated in FIG. 3, a rotational movement axis X and a rotational movement axis Y substantially perpendicular to the rotational movement axis X are alternately provided as rotational movement axes of the two adjacent pieces 50. The bending part 15 is capable of being bent in a total of four directions of upward-downward directions based on the rotational movement around the rotational movement axes X of the two adjacent pieces 50 and leftward-rightward directions based on the rotational movement around the rotational movement axes Y of the two adjacent pieces 50.

In addition, the maximum bending angle of the bending part 15 in the leftward-rightward directions and the maximum bending angle of the bending part 15 in the upward-downward directions may be the same as or different from each other. For example, the maximum bending angles in the upward-downward directions can be made relatively large by making the number of sets of two pieces 50 rotationally movable around the rotational movement axis X more than the number of sets of two pieces 50 rotationally movable around the rotational movement axis Y.

Additionally, the maximum rotational movement angles of respective sets of two pieces 50 rotationally movable around the rotational movement axis X may be the same as or different from each other, and the maximum rotational movement angle of each set can be set depending on a spacing Gx between the two pieces 50. Similarly, the maximum rotational movement angles of respective sets of two pieces 50 rotationally movable around the rotational movement axis Y may be the same as or different from each other, and the maximum rotational movement angle of each set can be set depending on a spacing Gy between the two pieces 50.

A pair of operating wires 22A corresponding to bending in the upward-downward directions and a pair of operating wires 22B corresponding to bending in the leftward-rightward directions are provided as the plurality of operating wires 22 (refer to FIG. 2). The pair of operating wires 22A and the pair of operating wires 22B reach the distal end part 14 from the operating part 11 through the insides of the plurality of pieces 50 and are fixed to the distal end sleeve 41, respectively. Additionally, the channel tube 43 that forms the treatment tool insertion channel 23 also reaches the distal end part 14 from the operating part 11 through the insides of the plurality of pieces 50 and is joined to the distal end rigid part 40.

Figure 4:
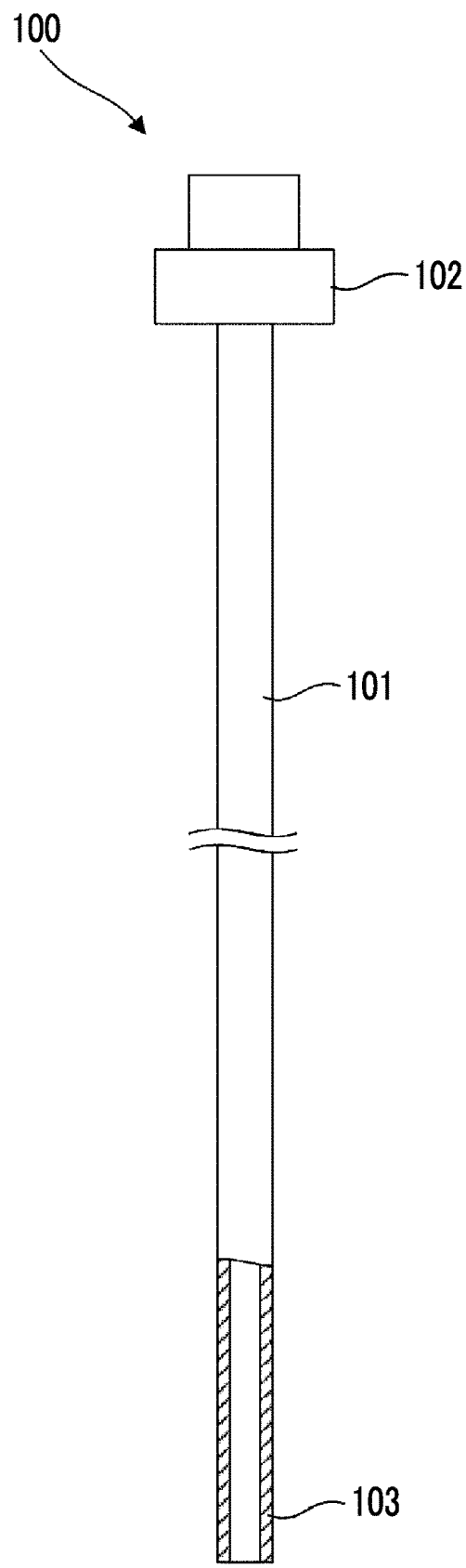
FIG. 4 is a plan view of an example of an endoscope aid for explaining the embodiment of the present invention.

FIG. 4 illustrates an example of the endoscope aid for explaining the embodiment of the present invention.

An endoscope aid 100 illustrated in FIG. 4 is attachably and detachably attached to the treatment tool insertion channel 23 of the endoscope 2. The endoscope aid 100 has a flexible tubular member 101 having a circular cross-sectional shape and a mouthpiece 102 coupled to a proximal end part of the tubular member 101. The tubular member 101 is inserted into the treatment tool insertion channel 23 through the opening of the inlet portion 24 of the treatment tool insertion channel 23. The mouthpiece 102 is attachably and detachably mounted on the inlet portion 24.

The distal end part 103 of the tubular member 101 reaches the outlet portion 25 of the treatment tool insertion channel 23 with the mouthpiece 102 mounted on the inlet portion 24 of the treatment tool insertion channel 23. In other words, the tubular member 101 has a length equal to or larger than a length ranging from at least an inlet-side end part of the outlet portion 25 of the treatment tool insertion channel 23 to an opening (inlet) of the inlet portion 24.

With reference to FIGS. 5 to 8, the outlet portion 25 of the treatment tool insertion channel 23 will be described.

As described above, the channel tube 43 constituting the treatment tool insertion channel 23 reaches the distal end part 14 of the insertion part 10 through the insides of the plurality of pieces 50 included in the bending part 15 of the insertion part 10 and is joined to the distal end rigid part 40 of the distal end part 14, and the inner hole of the channel tube 43 communicates with the through-hole 42 of the distal end rigid part 40. Although the channel tube 43 is bent in accordance with the bending of the bending part 15, the outlet portion 25 of the treatment tool insertion channel 23 is a portion that is maintained in the shape of a straight pipe irrespective of the bending of the bending part 15.

Figure 5:
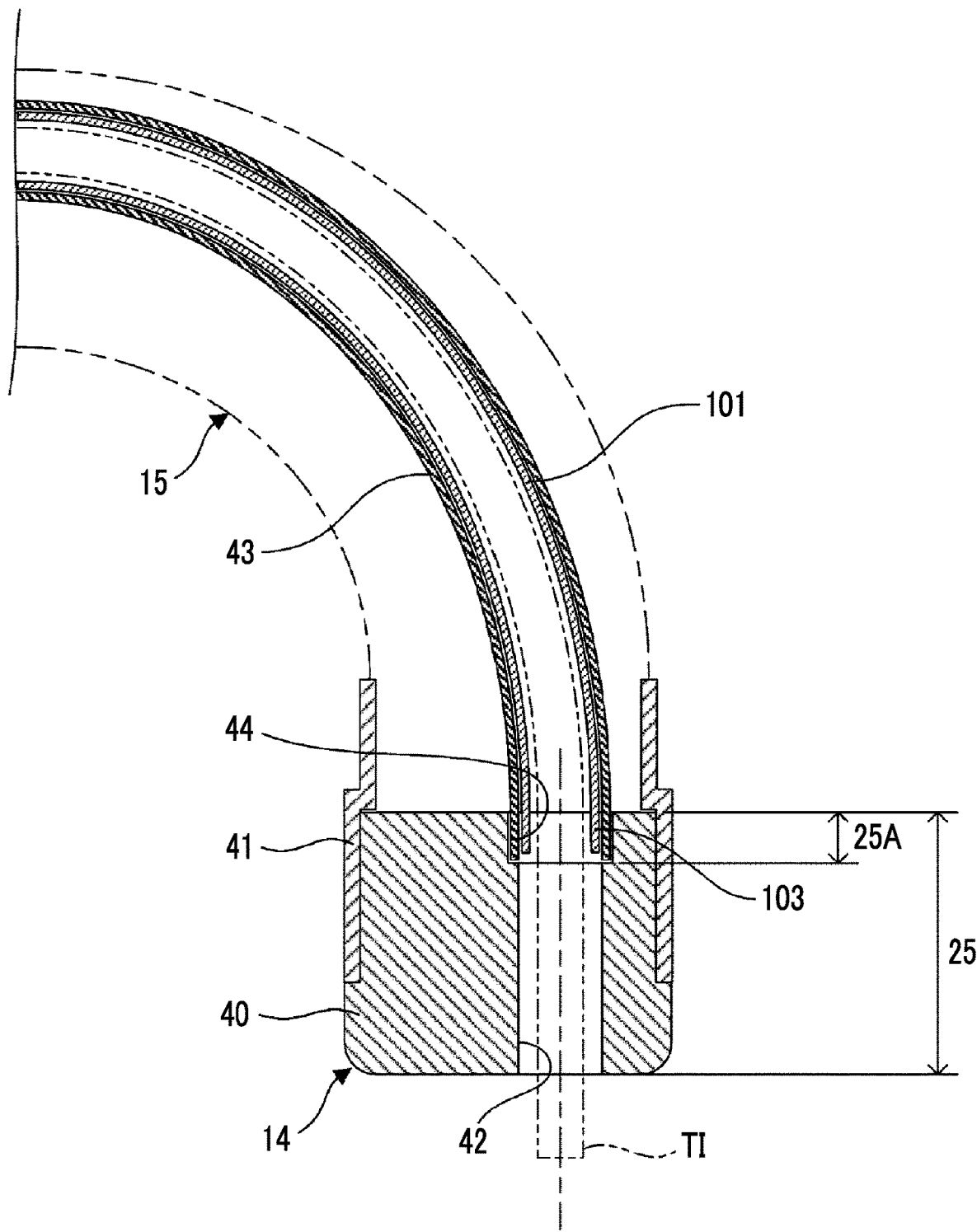
FIG. 5 is a cross-sectional view of an example of an outlet portion of a treatment tool insertion channel in a state where the endoscope aid of FIG. 4 is attached to the treatment tool insertion channel of the endoscope of FIG. 1.

In the example illustrated in FIG. 5, a fitting hole 44, which is coaxial with the through-hole 42 and has a larger diameter than the through-hole 42, is formed in a proximal end part of the distal end rigid part 40. A distal end of the channel tube 43 is internally fitted to the fitting hole 44 and is joined to the distal end rigid part 40 by bonding or the like. The through-hole 42 and the fitting hole 44 are maintained in the shape of a straight pipe irrespective of the bending of the bending part 15. In this case, the outlet portion 25 of the treatment tool insertion channel 23 is constituted of the through-hole 42 and the fitting hole 44, and an inlet-side end part 25A of the outlet portion 25 is constituted of the fitting hole 44.

Figure 6:
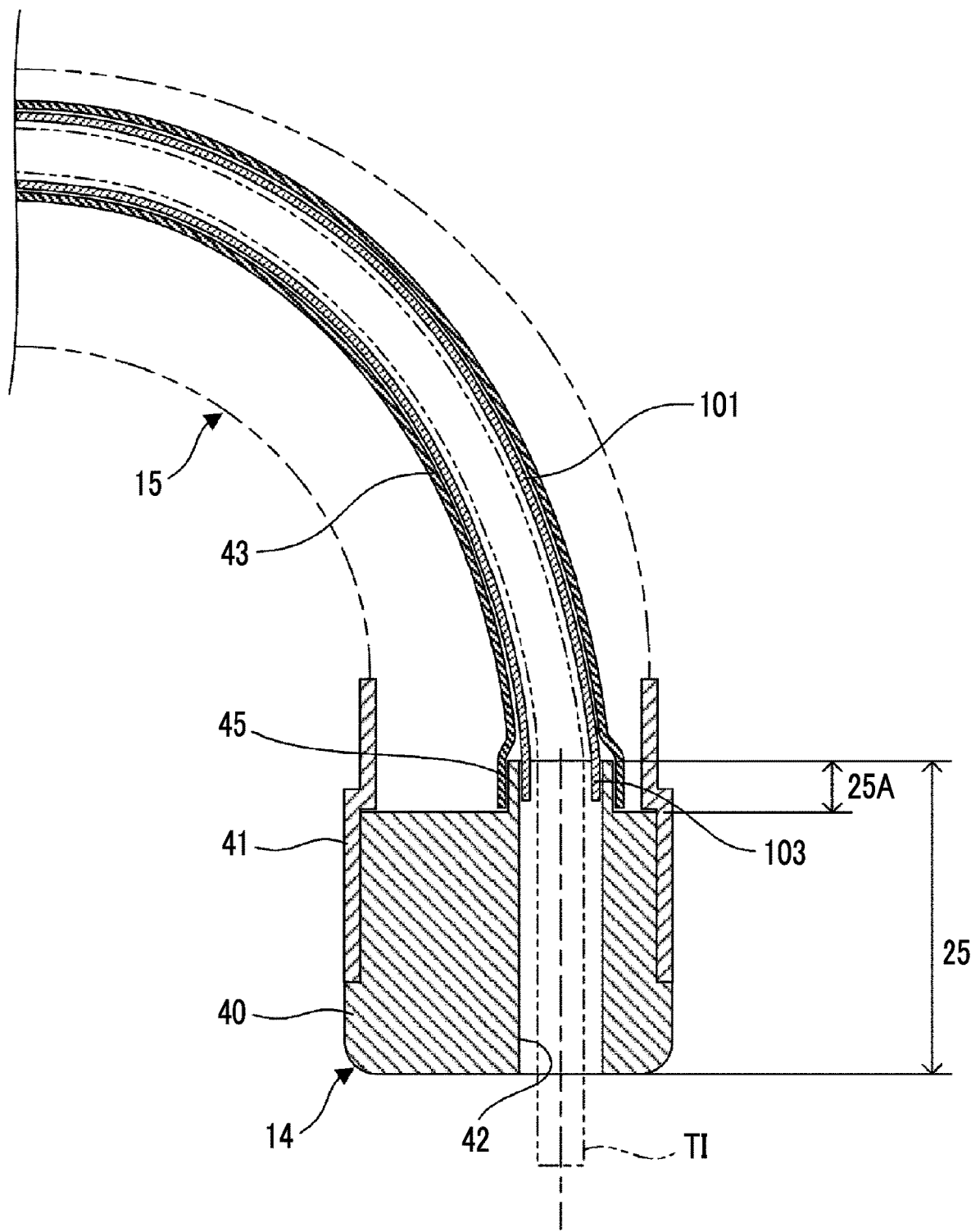
FIG. 6 is a cross-sectional view of another example of the outlet portion of the treatment tool insertion channel in the state where the endoscope aid of FIG. 4 is attached to the treatment tool insertion channel of the endoscope of FIG. 1.

In the example illustrated in FIG. 6, an annular protrusion 45, which is coaxial with the through-hole 42 and has the same internal diameter as the internal diameter of the through-hole 42, is formed in the proximal end part of the distal end rigid part 40 integrally with the distal end rigid part 40. The distal end of the channel tube 43 is externally fitted to the annular protrusion 45. The through-hole 42 and the annular protrusion 45 are maintained in the shape of a straight pipe irrespective of the bending of the bending part 15. In this case, the outlet portion 25 of the treatment tool insertion channel 23 is constituted of the through-hole 42 and the annular protrusion 45, and the inlet-side end part 25A of the outlet portion 25 is constituted of the annular protrusion 45.

Figure 7:
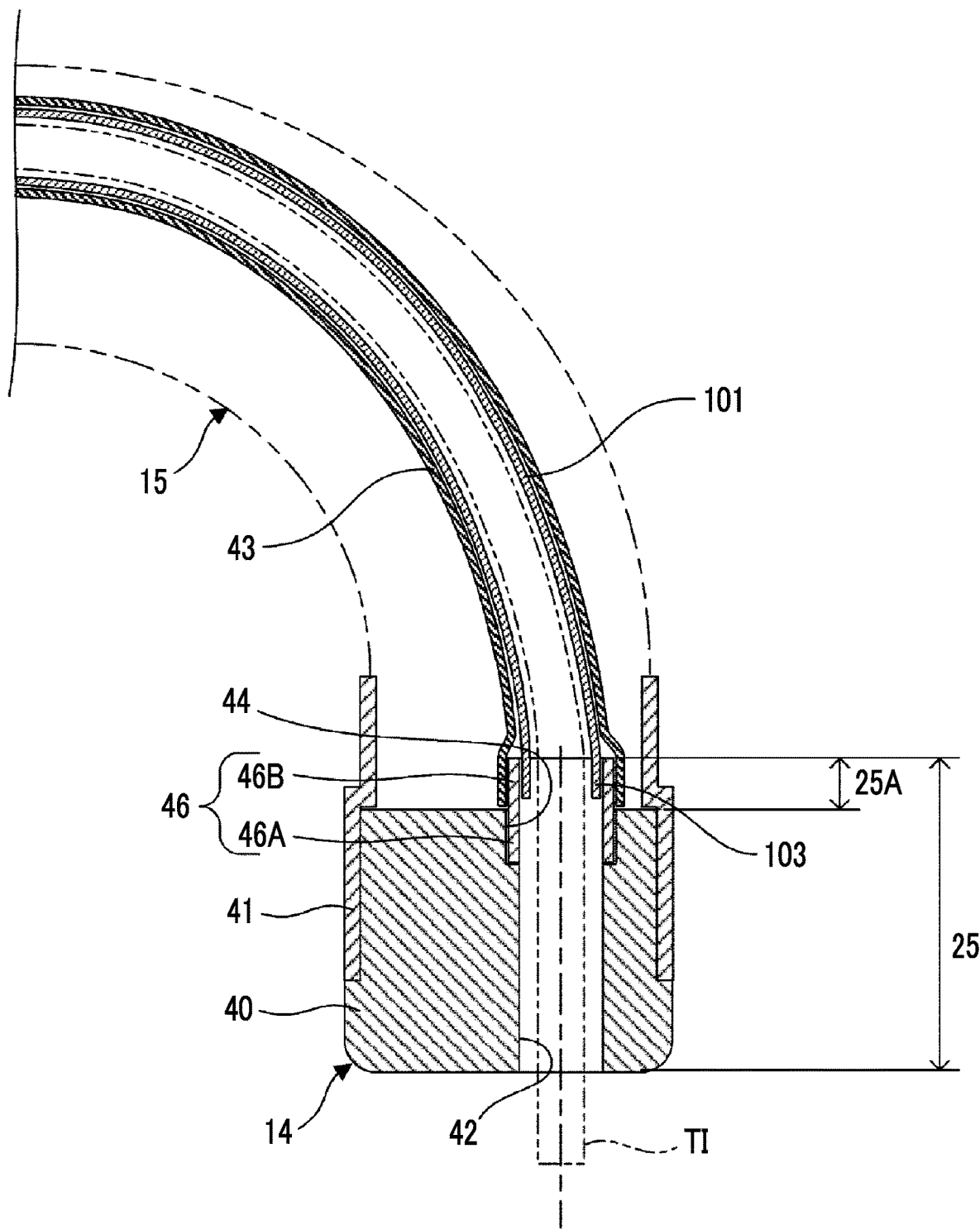
FIG. 7 is a cross-sectional view of still another example of the outlet portion of the treatment tool insertion channel in the state where the endoscope aid of FIG. 4 is attached to the treatment tool insertion channel of the endoscope of FIG. 1.

In the example illustrated in FIG. 7, a fitting hole 44, which is coaxial with the through-hole 42 and has a larger diameter than the through-hole 42, is formed in the proximal end part of the distal end rigid part 40, and a distal end part 46A of a hard connection pipe 46 that is a member separate from the distal end rigid part 40, is internally fitted the fitting hole 44. The distal end of the channel tube 43 is externally fitted to a proximal end part 46B of the connection pipe 46 protruding from the fitting hole 44. The through-hole 42, the fitting hole 44, and the connection pipe 46 are maintained in the shape of a straight pipe irrespective of the bending of the bending part 15. In this case, the outlet portion 25 of the treatment tool insertion channel 23 is constituted of the through-hole 42, the fitting hole 44, and the connection pipe 46 and an inlet-side end part 25A of the outlet portion 25 is constituted of the proximal end part 46B of the connection pipe 46.

Figure 8:
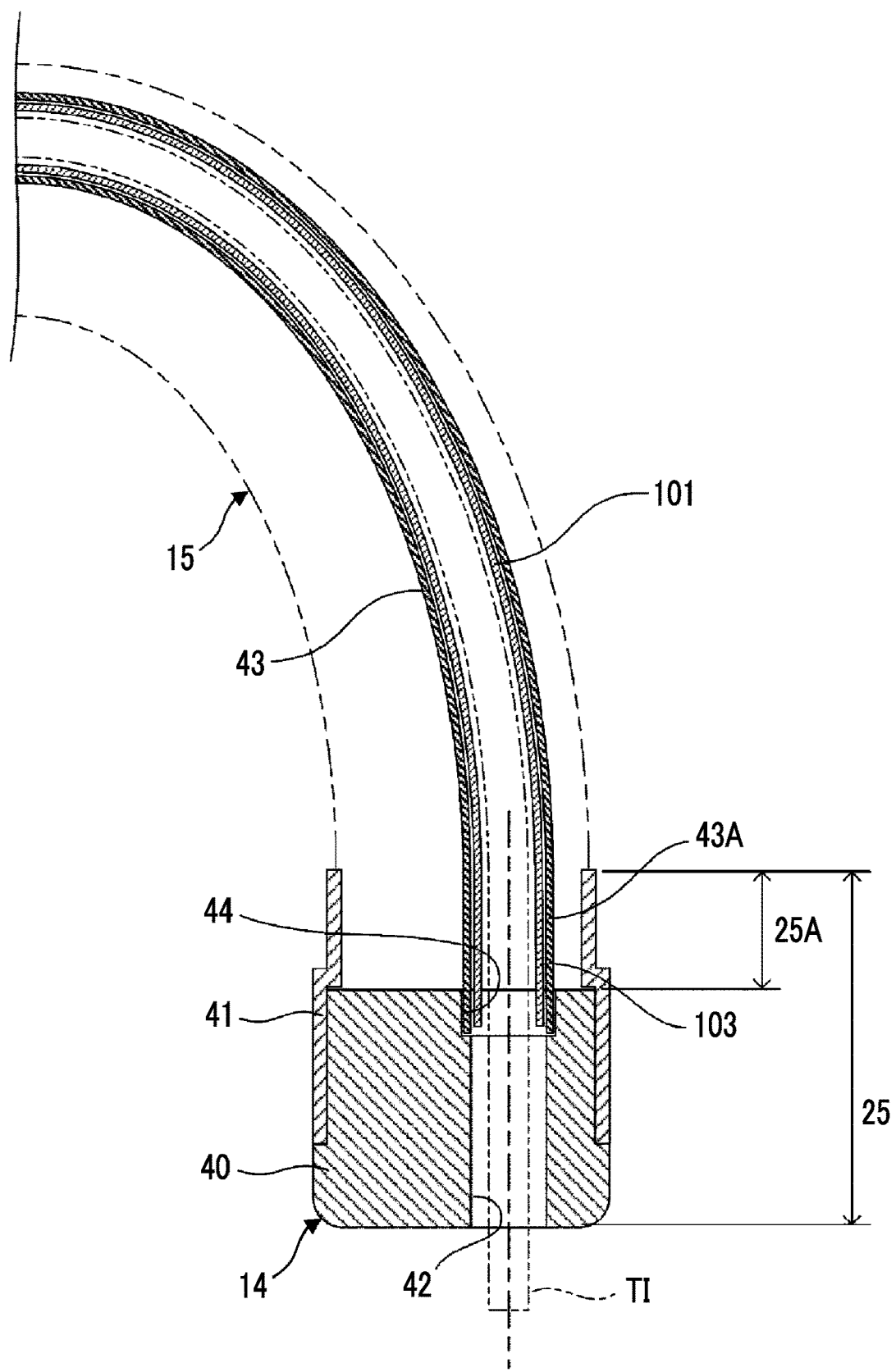
FIG. 8 is a cross-sectional view of a still further example of the outlet portion of the treatment tool insertion channel in the state where the endoscope aid of FIG. 4 is attached to the treatment tool insertion channel of the endoscope of FIG. 1.

In the example illustrated in FIG. 8, the maximum rotational movement angle of a set of two adjacent pieces 50 disposed nearest to the distal end part 14 side among the plurality of pieces 50 (refer to FIG. 3) included in the bending part 15 is extremely small, and a distal end part 43A of the channel tube 43 disposed inside the distal end sleeve 41 of the distal end part 14 is maintained in the shape of a straight pipe irrespective of the bending of the bending part 15. The outlet portion 25 of the treatment tool insertion channel 23 is constituted of the through-hole 42, the fitting hole 44, and the distal end part 43A of the channel tube 43, and the inlet-side end part 25A of the outlet portion 25 is constituted of the distal end part 43A of the channel tube 43.

In addition, whether or not the channel tube 43 is in the shape of a straight pipe can be evaluated depending on the straightness of the channel tube 43 in the longitudinal axis, and in a case where the straightness of a portion to be evaluated in the longitudinal axis is 10% or less of the internal diameter of the channel tube 43, the portion to be evaluated is in the shape of a straight pipe. Additionally, in a case where two or more sets of two pieces 50 of which the maximum rotational movement angle is extremely small are continuously provided from the distal end part 14 side, there is a case where the outlet portion 25 reaches the insides of one or a plurality of pieces 50 disposed on the distal end part 14 side.

The distal end part 103 of the tubular member 101 has an outer periphery that is in sliding contact with an inner peripheral surface of the outlet portion 25 of the treatment tool insertion channel 23. In the tubular member 101 having a circular cross-sectional shape, an outer peripheral surface of the distal end part 103 is in sliding contact with the inner peripheral surface of the outlet portion 25. In a case where the inner peripheral surface of the outlet portion 25 and the outer peripheral surface of the distal end part 103 are in sliding contact with each other, it is desirable that the internal diameter of the outlet portion 25 and the external diameter of the distal end part 103 have a so-called clearance fitting relationship (Internal diameter of outlet portion 25>External diameter of distal end part 103). However, in a case where the material of the treatment tool insertion channel 23 is flexible, a tight-fitting relationship (Internal diameter of outlet portion 25<External diameter of distal end part 103) may be established. As the outer peripheral surface of the distal end part 103 of the tubular member 101 and the inner peripheral surface of the outlet portion 25 of the treatment tool insertion channel 23 are in sliding contact with each other, the disposition of the distal end part 103 at the outlet portion 25 is stable. A central axis of an inner hole of the outlet portion 25, which is kept in the shape of a straight pipe regardless of the bending of the bending part 15, and a central axis of an inner hole of the distal end part 103 are parallel to each other and coincide with each other in the present example.

The above endoscope aid 100 is used in combination with a treatment tool TI with a smaller size than the internal diameter of the treatment tool insertion channel 23. The treatment tool TI is, for example, a puncturing needle, high-frequency scissors forceps, a high-frequency knife, bipolar hemostatic forceps, a clip, a collection net, or the like. First, the tubular member 101 of the endoscope aid 100 is inserted into the treatment tool insertion channel 23, and the distal end part 103 of the tubular member 101 is disposed at the outlet portion 25 of the treatment tool insertion channel 23. Next, the treatment tool TI is inserted into the tubular member 101 through the opening of the mouthpiece 102 of the endoscope aid 100.

The treatment tool TI inserted into the tubular member 101 is guided to the distal end part 103 of the tubular member 101 by the tubular member 101 and protrudes from the distal end part 14 of the insertion part 10 through the opening of the distal end part 103 and further through the opening of the outlet portion 25 of the treatment tool insertion channel 23. Since the treatment tool TI protrudes onto the central axis of the inner hole of the distal end part 103 and the central axis of the inner hole of the distal end part 103 and the central axis of the inner hole of the outlet portion 25 are parallel to each other, the treatment tool TI protrudes along the central axis of the inner hole of the outlet portion 25. Accordingly, the disposition of the treatment tool TI is stable.

In addition, in the examples that are respectively illustrated in FIGS. 5 to 8, the distal end part 103 of the tubular member 101 is disposed at the inlet-side end part 25A of the outlet portion 25 of the treatment tool insertion channel 23. However, for example, the distal end part 103 may reach the opening of the outlet portion 25 or may protrude from the opening of the outlet portion 25.

As the outer peripheral surface of the distal end part 103 of the tubular member 101 is in sliding contact with the inner peripheral surface of the outlet portion 25 of the treatment tool insertion channel 23, the disposition of the distal end part 103 at the outlet portion 25 is stable. On the other hand, the opening of the outlet portion 25 leading to the suction tube 26 (refer to FIG. 2) is blocked by the distal end part 103. Thus, the tubular member 101 has a communication part that allows the opening of the outlet portion 25 and the suction tube 26 to communicate with each other.

Figure 9:
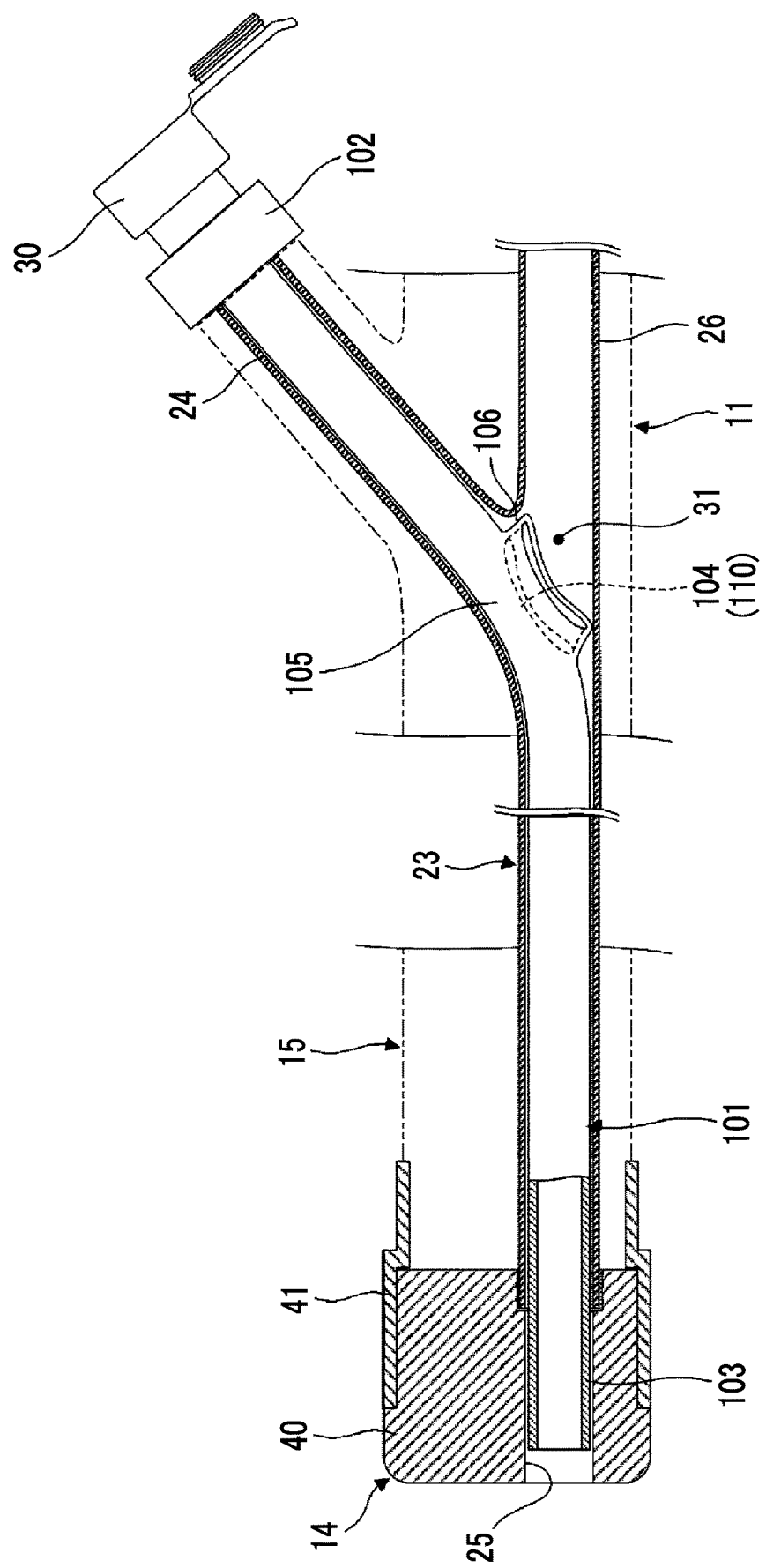
FIG. 9 is a schematic view of an example of a communication part of the endoscope aid of FIG. 4.

FIG. 9 illustrates the configuration of the communication part of the tubular member 101.

The communication part 104 has a cutout 110 that penetrates the tubular member 101 from the inner peripheral surface of the tubular member 101 to the outer peripheral surface thereof. The cutout 110 is provided at an intermediate part 105 of the tubular member 101 disposed at a joining part 31 where the treatment tool insertion channel 23 and the suction tube 26 join each other. Also, as the tubular member 101 is appropriately rotated around the longitudinal axis of the tubular member 101, the cutout 110 is disposed so as to overlap an opening of the suction tube 26 at the joining part 31.

As the cutout 110 is disposed so as to overlap the opening of the suction tube 26 at the joining part 31, the opening of the outlet portion 25 of the treatment tool insertion channel 23 and the suction tube 26 communicate with each other through the inner hole and the cutout 110 of the tubular member 101. Accordingly, suction is possible even in a state where the tubular member 101 is inserted into the treatment tool insertion channel 23. A forceps valve 30 having an on-off valve is mounted on the mouthpiece 102, and during suction, the opening of the mouthpiece 102 is closed by the forceps valve 30, and the internal pressure of the tubular member 101 becomes a negative pressure. In addition, the mouthpiece 102 may have an on-off valve.

In the present example, the cutout 110 is formed in a circular shape, and the hole diameter of the cutout 110 is equal to or larger than the internal diameter of the tubular member 101. In addition, the shape of the cutout 110 is not limited to the circular shape and may be, for example, a non-circular shape such as a rectangular shape. In the case of the non-circular shape, the minimum dimension of the cutout 110 is equal to or larger than the internal diameter of the tubular member 101. As the minimum dimension of the cutout 110 is equal to or larger than the internal diameter of the tubular member 101, the suction force can be maintained.

Preferably, as illustrated in FIG. 9, the endoscope aid 100 includes a positioning part 106 that aligns the rotational position of the tubular member 101 around the longitudinal axis with a predetermined position where the cutout 110 overlaps the opening of the suction tube 26 at the joining part 31. The positioning part 106 is a protrusion provided on the outer peripheral surface of the tubular member 101 and is formed in an annular shape along the edge of the cutout 110. In a case where the tubular member 101 is not at the predetermined position, the positioning part 106 is elastically deformed so as to fall inside the cutout 110, for example, and in a case where the tubular member 101 is disposed at the predetermined position, the positioning part 106 is restored from the elastic deformation and engaged with an inner edge of the opening of the suction tube 26. Also, as the positioning part 106 is engaged with the inner edge of the opening of the suction tube 26, the tubular member 101 is positioned at the predetermined position.

In addition, the positioning part may be constituted of, for example, an index formed by printing, engraving, or the like on the outer periphery of the inlet portion 24 of the treatment tool insertion channel 23 and the outer periphery of the mouthpiece 102 of the endoscope aid 100. The index is, for example, a figure, a symbol, or the like. As the indexes of the inlet portion 24 and the mouthpiece 102 are lined up, the rotational position of the tubular member 101 around the longitudinal axis is determined.

Figure 10:
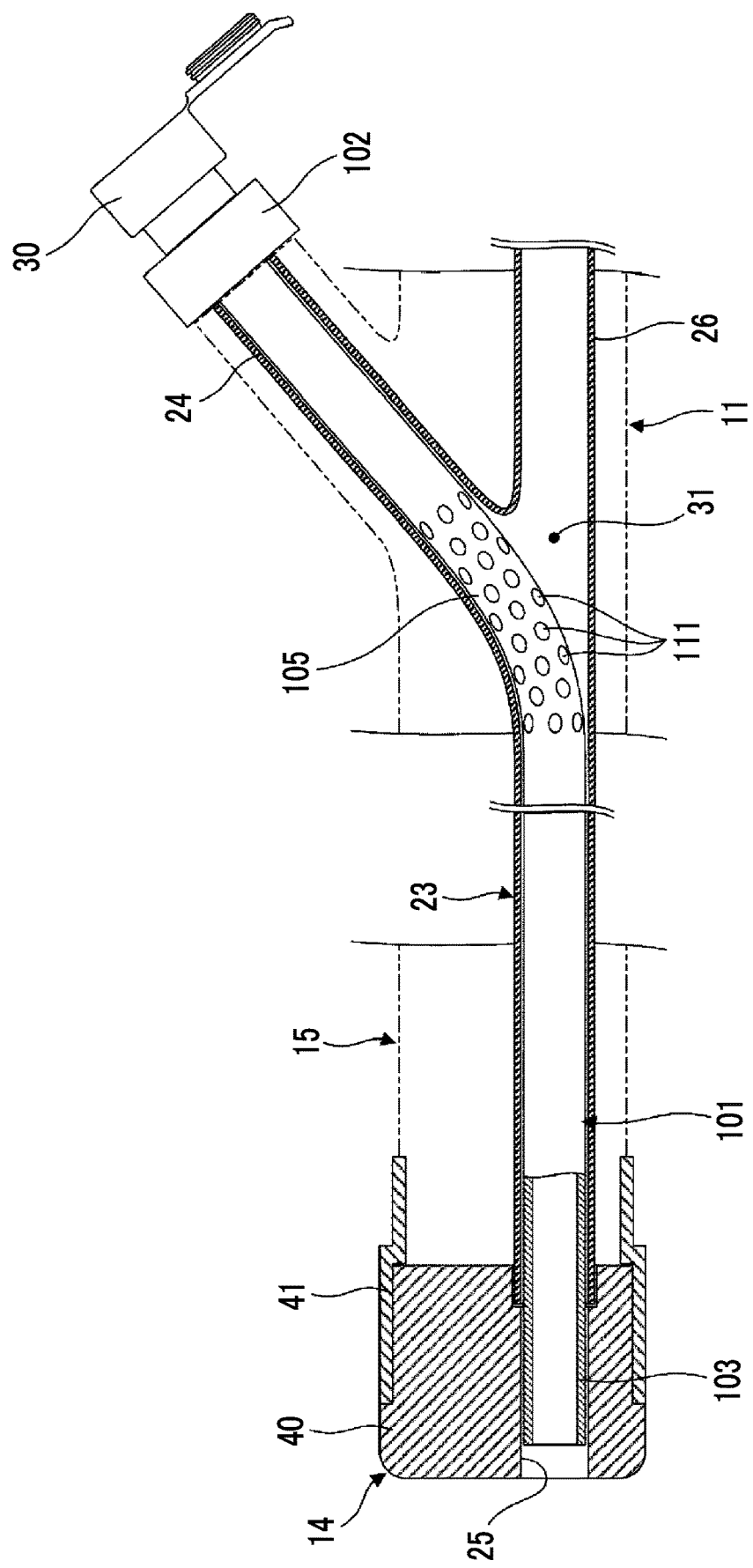
FIG. 10 is a schematic view of a modification example of the communication part of the endoscope aid of FIG. 4.

FIG. 10 illustrates a modification example of the communication part 104.

Figure 11:
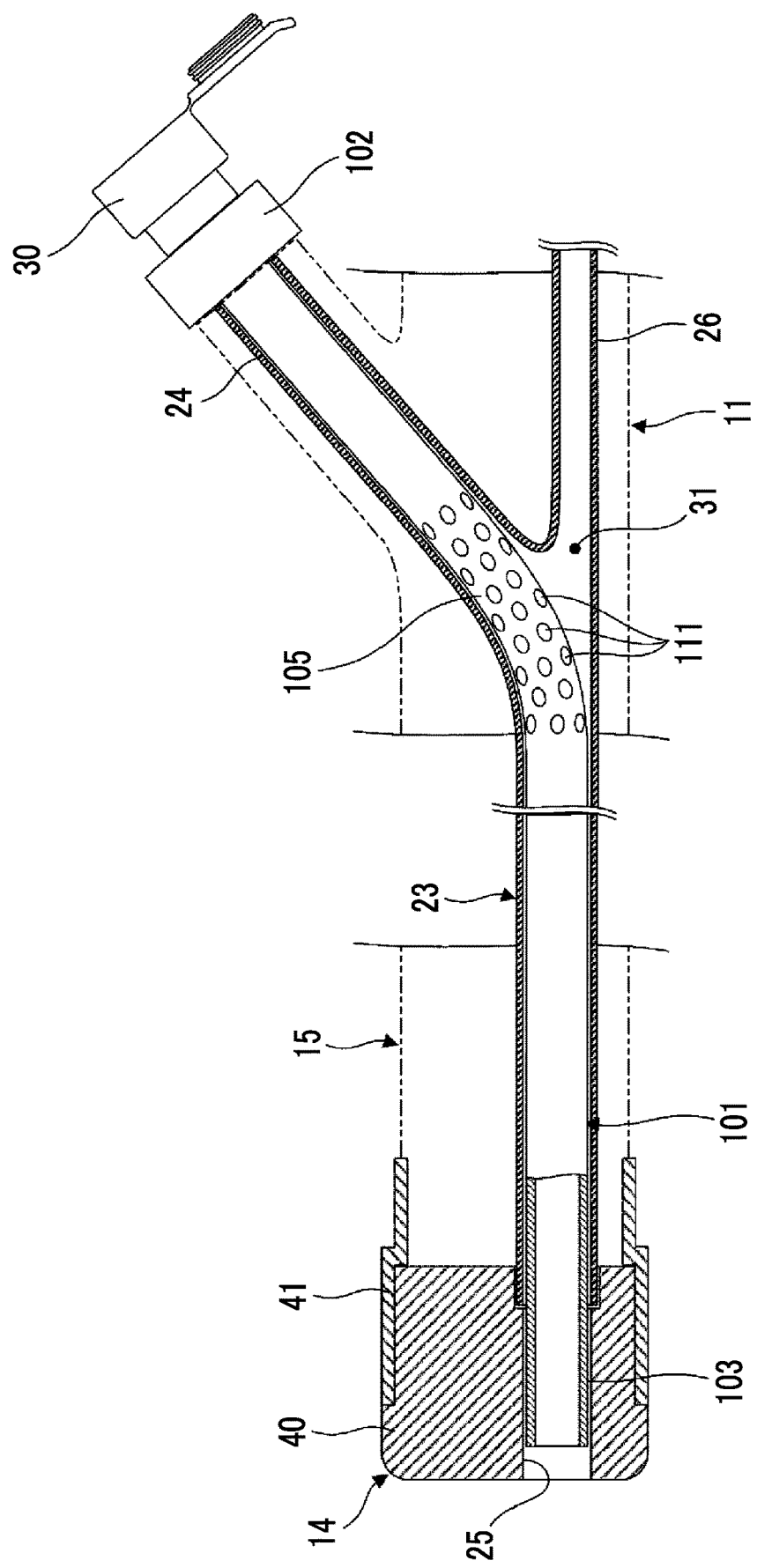
FIG. 11 is a schematic view of a preferred form of the communication part of the endoscope aid of FIG. 10.

In the example illustrated in FIG. 10, the communication part 104 has the plurality of cutouts 111, and the maximum dimension of each of the cutouts 111 is less than the internal diameter of the tubular member 101. As the plurality of the cutouts 111 are disposed so as to overlap the opening of the suction tube 26 at the joining part 31, even in a case where the maximum dimension of each of the cutouts 111 is less than the internal diameter of the tubular member 101, a decrease in suction force is suppressed. Also, as the maximum dimension of each of the cutouts 111 is less than the internal diameter of the tubular member 101, a relatively large solid substance suctioned into the inner hole of the tubular member 101 can be retained in the cutout 111 and easily collected by the tubular member 101. As illustrated in FIG. 11, in a case where the internal diameter of the suction tube 26 is smaller than the internal diameter of the treatment tool insertion channel 23, the maximum dimension of each of the cutouts 111 is preferably less than the internal diameter of the suction tube 26. Accordingly, the suction tube 26 can be prevented from being clogged with a relatively large solid substance suctioned into the inner hole of the tubular member 101.

Additionally, preferably, as illustrated in FIGS. 10 and 11, the plurality of cutouts 111 are provided so as to be dispersed over the entire circumference of the intermediate part 105 of the tubular member 101. In this case, at least one cutout 111 is disposed so as to overlap the opening of the suction tube 26 at the joining part 31 regardless of the rotational position of the tubular member 101 around the longitudinal axis. Accordingly, the attachment of the endoscope aid 100 to the treatment tool insertion channel 23 is facilitated.

Figure 12:
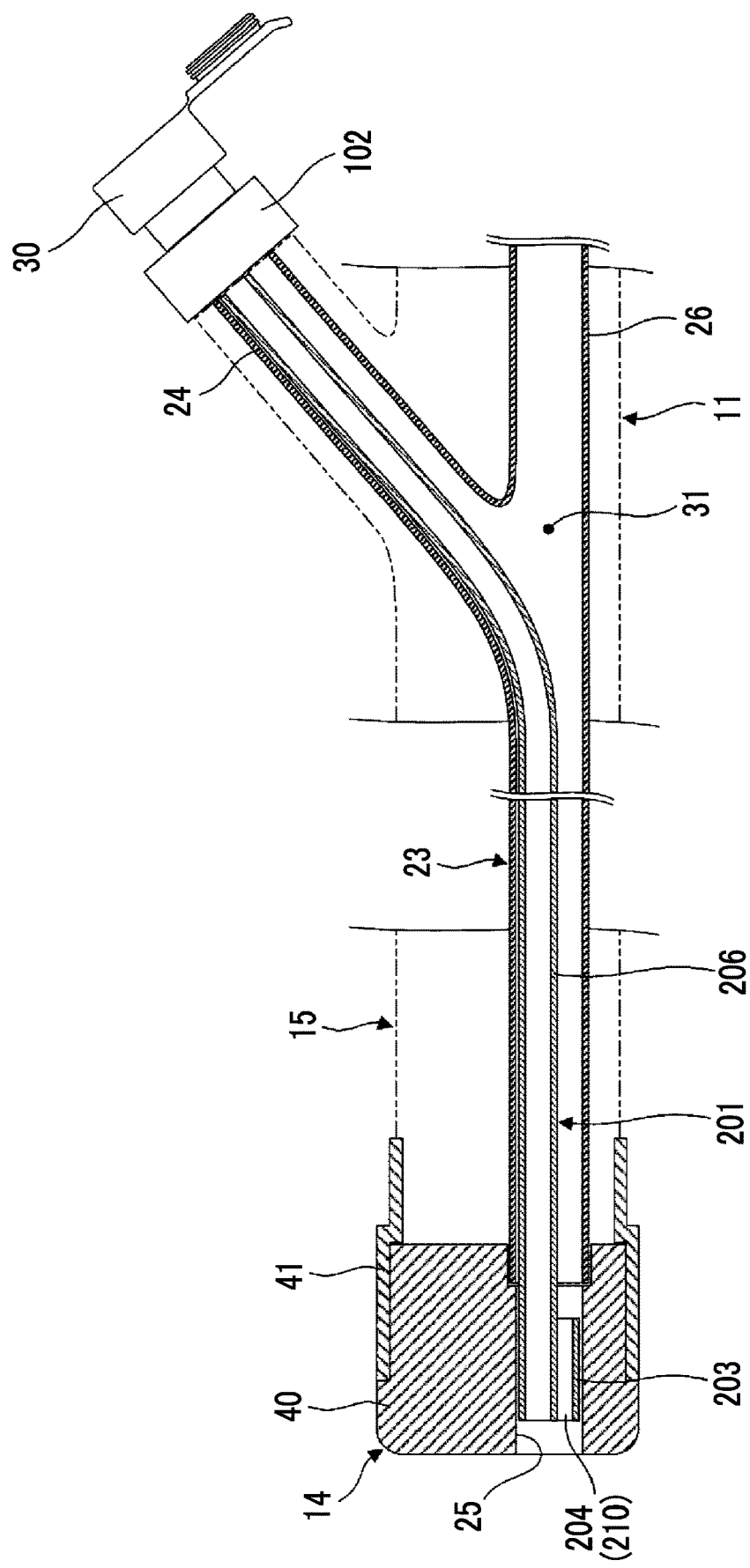
FIG. 12 is a cross-sectional view of another example of the endoscope aid for explaining the embodiment of the present invention.

FIG. 12 illustrates another example of the endoscope aid for explaining the embodiment of the present invention.

An endoscope aid 200 illustrated in FIG. 12 is attachably and detachably attached to the treatment tool insertion channel 23 of the endoscope 2. An endoscope aid 200 has a flexible tubular member 201 having a circular cross-sectional shape and a mouthpiece 202 coupled to a proximal end part of the tubular member 201. The tubular member 201 has a length equal to or larger than a length ranging from at least the inlet-side end part of the outlet portion 25 of the treatment tool insertion channel 23 to the opening of the inlet portion 24. With the mouthpiece 202 mounted on the inlet portion 24, the distal end part 203 of the tubular member 201 reaches the outlet portion 25, and the outer peripheral surface of the distal end part 203 is in sliding contact with the inner peripheral surface of the outlet portion 25. The portion of the tubular member 201 other than the distal end part 203 is a smaller-diameter part 206 that is thinner than the distal end part 203.

The endoscope aid 200 has a communication part 204 that allows the opening of the outlet portion 25 of the treatment tool insertion channel 23 and the suction tube 26 to communicate with each other, and the communication part 204 has a through-hole 210 formed at the distal end part 203 of the tubular member 201. The through-hole 210 penetrates the distal end part 203 in the axial direction and is connected to a gap formed between an inner peripheral surface of the treatment tool insertion channel 23 and an outer peripheral surface of the smaller-diameter part 206 of the tubular member 201. The opening of the outlet portion 25 and the suction tube 26 communicate with each other through the through-hole 210 and further through the gap. Accordingly, suction is possible even in a state where the tubular member 201 is inserted into the treatment tool insertion channel 23.

As described above, the endoscope aid disclosed in the present specification is an endoscope aid to be attachably and detachably attached to a treatment tool insertion channel of an endoscope where a suction tube joins. The endoscope aid comprises a flexible tubular member having a length equal to or larger than a length ranging from at least an inlet-side end part of an outlet portion of the treatment tool insertion channel, which is maintained in a shape of a straight pipe regardless of bending of a bending part of the endoscope, to an inlet of the treatment tool insertion channel. The tubular member has a distal end part that has an outer periphery in sliding contact with an inner peripheral surface of the outlet portion of the treatment tool insertion channel and is disposed at the outlet portion, and a communication part that allows an outlet of the treatment tool insertion channel and the suction tube to communicate with each other.

Additionally, in the endoscope aid disclosed in the present specification, the communication part has one or more cutouts that penetrate the tubular member from an inner peripheral surface of the tubular member to an outer peripheral surface thereof.

Additionally, in the endoscope aid disclosed in the present specification, the tubular member has an intermediate part disposed at a joining part where the treatment tool insertion channel and the suction tube join each other, and the cutout is provided at the intermediate part of the tubular member.

Additionally, in the endoscope aid disclosed in the present specification, a minimum dimension of the cutout is equal to or larger than an internal diameter of the tubular member.

Additionally, in the endoscope aid disclosed in the present specification, a plurality of the cutouts are provided at the intermediate part of the tubular member, and a maximum dimension of each of the plurality of cutouts is less than an internal diameter of the tubular member.

Additionally, in the endoscope aid disclosed in the present specification, the internal diameter of the suction tube is smaller than an internal diameter of the treatment tool insertion channel, and the maximum dimension of each of the plurality of cutouts is less than the internal diameter of the suction tube.

Additionally, the endoscope aid disclosed in the present specification comprises a positioning part that aligns a rotational position around a longitudinal axis of the tubular member with a position of the joining part where at least one cutout overlaps an opening of the suction tube.

Additionally, in the endoscope aid disclosed in the present specification, the positioning part is a protrusion provided on the outer peripheral surface of the tubular member and engages with an inner edge of the opening of the suction tube.

Additionally, in the endoscope aid disclosed in the present specification, the plurality of cutouts are provided so as to be dispersed over an entire circumference of the intermediate part.

Additionally, in the endoscope aid disclosed in the present specification, a portion of the tubular member other than the distal end part is a smaller-diameter part thinner than the distal end part, the communication part has a through-hole that penetrates the distal end part in an axial direction, and the through-hole is connected to a gap formed between an inner peripheral surface of the treatment tool insertion channel and an outer peripheral surface of the smaller-diameter part.

Additionally, an endoscope disclosed in the present specification comprises a treatment tool insertion channel to which the endoscope aid is attachable.

EXPLANATION OF REFERENCES

1: endoscope system
2: endoscope
3: light source device
4: processor unit
5: suction pump
6: monitor
10: insertion part
11: operating part
12: universal cord
13: connector
14: distal end part
15: bending part
16: flexible part
17: imaging unit
18A, 18C: operation button
18B: operating knob
20: light guide
21: electrical cable
22, 22A, 22B: operating wire
23: treatment tool insertion channel
24: inlet portion of treatment tool insertion channel
25: outlet portion of treatment tool insertion channel
25A: inlet-side end part of the outlet portion of the treatment tool insertion channel
26: suction tube
27: valve
28, 102, 202: mouthpiece
29: connection tube
30: forceps valve
31: joining part between treatment tool insertion channel and suction tube
40: distal end rigid part
41: distal end sleeve
42, 210: through-hole
43: channel tube
43A: distal end part of channel tube
44: fitting hole
45: annular protrusion
46: connection pipe
46A: distal end part of connection pipe
46B: proximal end part of connection pipe
50: piece
51: shaft member
100, 200: endoscope aid
101, 201: tubular member
103, 203: distal end part of tubular member
104, 204: communication part
105: intermediate part of tubular member
106: positioning part
110, 111: cutout
206: smaller-diameter part of tubular member
Gx, Gy: spacing
TI: treatment tool
X, Y: rotational movement axis

What is claimed is:

1. An endoscope aid to be attachably and detachably attached to a treatment tool insertion channel of an endoscope where a suction tube joins, the endoscope aid comprising:
a flexible tubular member having a length equal to or larger than a length ranging from at least an inlet-side end part of an outlet portion of the treatment tool insertion channel, which is maintained in a shape of a straight pipe regardless of bending of a bending part of the endoscope, to an inlet of the treatment tool insertion channel,
wherein the tubular member includes
a distal end part that has an outer periphery in sliding contact with an inner peripheral surface of the outlet portion of the treatment tool insertion channel and is disposed at the outlet portion, and
a communication part that allows an outlet of the treatment tool insertion channel and the suction tube to communicate with each other;
wherein the communication part has a cutout that penetrates the tubular member from an inner peripheral surface of the tubular member to an outer peripheral surface thereof,
wherein the tubular member has an intermediate part disposed at a joining part where the treatment tool insertion channel and the suction tube join each other, and
the cutout is provided at the intermediate part of the tubular member,
wherein a minimum dimension of the cutout is equal to or larger than an internal diameter of the tubular member.

2. The endoscope aid according to claim 1, further comprising:
a positioning part that aligns a rotational position around a longitudinal axis of the tubular member with a position of the joining part where the cutout overlaps an opening of the suction tube.

3. The endoscope aid according to claim 2,
wherein the positioning part is a protrusion provided on the outer peripheral surface of the tubular member and engages with an inner edge of the opening of the suction tube.

4. An endoscope comprising:
a treatment tool insertion channel to which the endoscope aid according to claim 1 is attachable.

5. An endoscope aid to be attachably and detachably attached to a treatment tool insertion channel of an endoscope where a suction tube joins, the endoscope aid comprising:
a flexible tubular member having a length equal to or larger than a length ranging from at least an inlet-side end part of an outlet portion of the treatment tool insertion channel, which is maintained in a shape of a straight pipe regardless of bending of a bending part of the endoscope, to an inlet of the treatment tool insertion channel, wherein the tubular member includes
a distal end part that has an outer periphery in sliding contact with an inner peripheral surface of the outlet portion of the treatment tool insertion channel and is disposed at the outlet portion, and
a communication part that allows an outlet of the treatment tool insertion channel and the suction tube to communicate with each other;
wherein the communication part has a plurality of cutouts that penetrate the tubular member from an inner peripheral surface of the tubular member to an outer peripheral surface thereof,
wherein the tubular member has an intermediate part disposed at a joining part where the treatment tool insertion channel and the suction tube join each other, and
wherein the plurality of cutouts are provided at the intermediate part of the tubular member, and
a maximum dimension of each of the plurality of cutouts is less than an internal diameter of the tubular member.

6. The endoscope aid according to claim 5, wherein an internal diameter of the suction tube is smaller than an internal diameter of the treatment tool insertion channel, and
the maximum dimension of each of the plurality of cutouts is less than the internal diameter of the suction tube.

7. The endoscope aid according to claim 6, wherein the plurality of cutouts are provided so as to be dispersed over an entire circumference of the intermediate part.

8. The endoscope aid according to claim 5, wherein the plurality of cutouts are provided so as to be dispersed over an entire circumference of the intermediate part.

9. An endoscope comprising:
a treatment tool insertion channel to which the endoscope aid according to claim 5 is attachable.

10. An endoscope aid to be attachably and detachably attached to a treatment tool insertion channel of an endoscope where a suction tube joins, the endoscope aid comprising:
a flexible tubular member having a length equal to or larger than a length ranging from at least an inlet-side end part of an outlet portion of the treatment tool insertion channel, which is maintained in a shape of a straight pipe regardless of bending of a bending part of the endoscope, to an inlet of the treatment tool insertion channel,
wherein the tubular member includes
a distal end part that has an outer periphery in sliding contact with an inner peripheral surface of the outlet portion of the treatment tool insertion channel and is disposed at the outlet portion, and
a communication part that allows an outlet of the treatment tool insertion channel and the suction tube to communicate with each other,
wherein a portion of the tubular member other than the distal end part is a smaller-diameter part thinner than the distal end part,
the communication part has a through-hole that penetrates the distal end part in an axial direction, and
the through-hole is connected to a gap formed between an inner peripheral surface of the treatment tool insertion channel and an outer peripheral surface of the smaller-diameter part.

11. An endoscope comprising:
a treatment tool insertion channel to which the endoscope aid according to claim 10 is attachable.

* * * * *